(12) United States Patent
Bhimapaka et al.

(10) Patent No.: US 6,566,528 B1
(45) Date of Patent: May 20, 2003

(54) 1-(2-CHLORO-5-METHYL-3-PYRIDYLMETHYL)-2-NITROIMINOIMIDAZOLIDINE AND PROCESS FOR THE PREPARATION THEREOF

(75) Inventors: Chinaraju Bhimapaka, Andhra Pradesh (IN); Vaidya Jayathirtha Rao, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/984,456

(22) Filed: Oct. 30, 2001

(51) Int. Cl.7 ............................................. C07D 401/06
(52) U.S. Cl. ................................................... 546/274.7
(58) Field of Search ...................... 546/274.7

(56) References Cited

U.S. PATENT DOCUMENTS

| | | | |
|---|---|---|---|
| 4,849,432 A | * 7/1989 | Shiokawa et al. | 514/341 |
| 5,165,934 A | * 11/1992 | Wada et al. | 514/226.8 |
| 5,302,605 A | * 4/1994 | Kristiansen et al. | 514/341 |
| 5,521,176 A | * 5/1996 | Wada et al. | 514/226.8 |
| 5,674,520 A | * 10/1997 | Mete et al. | 514/226.8 |
| 6,307,053 B1 | * 10/2001 | Yeh et al. | 514/341 |

FOREIGN PATENT DOCUMENTS

| | | |
|---|---|---|
| EP | 0 192 060 A1 | 8/1986 |
| EP | 0 212 600 A2 | 3/1987 |
| EP | 0 483 052 A1 | 4/1992 |

OTHER PUBLICATIONS

CA 134:127235 Kagabu et al. 2000.*
CA 89:54095, Shiokawa et al. 1990.*

* cited by examiner

*Primary Examiner*—Jane Fan
(74) *Attorney, Agent, or Firm*—Burns, Doane, Swecker & Mathis, L.L.P.

(57) ABSTRACT

The present invention relates to 1-(2-chloro-5-methyl-3-pyridylmethyl)-2-nitroiminoimidazolidine of the formula 1, a novel compound of class nitroimino pyridyl derivatives and to a process for the preparation thereof

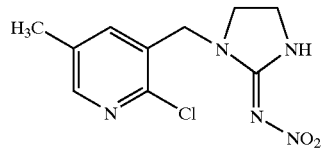

Formula 1

9 Claims, No Drawings

1-(2-CHLORO-5-METHYL-3-PYRIDYLMETHYL)-2-NITROIMINOIMIDAZOLIDINE AND PROCESS FOR THE PREPARATION THEREOF

FIELD OF THE INVENTION

The present invention relates to 1-(2-chloro-5-methyl-3-pyridylmethyl)-2-nitroiminoimidazolidine of the formula 1 given below and to process for the preparation thereof.

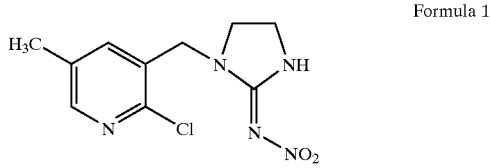

Formula 1

1-(2-chloro-5-methyl-3-pyridylmethyl)-2-nitroiminoimidazolidine of the formula 1 is a novel compound of class nitroimino pyridyl derivatives. The present invention also relates to a process for the preparation of 1-(2-chloro-5-methyl-3-pyridylmethyl)-2-nitroiminoimidazolidine using 2-chloro-3-chloromethyl-5-methylpyridine and 2-nitroimino-1,3-diazacyclopentane in various solvents using a base under appropriate conditions of mole ratio, time, temperature and work up procedure with high yields and selectivity.

BACKGROUND OF THE INVENTION 1-(6-chloronicotinyl)-2-nitroiminoimidazolidine and related compounds are reported as effectively controlling hemiptera, other sucking insects and against green rice leaf hopper [Biosci. Biotech. Biochem, 56(8), 1364 & 56(2), 364, 1992]. Structural modification in the 6-chloropyridyl and introduction of five membered hetero cyclic compounds are reported as insecticidal compounds [Biosci. Biotech. Biochem., 57(1), 127, 1993]. 1-(2-chloro-5-pyridylmethyl) 2-nitoiminoimidazolidine (Imidacloropid/Confidor) is a potent insecticide (EP 0192061, 1990 and Angew.Chem-.Int.Ed. 39, 1724, 2000) and acts at the nicotinic acetylcholine receptor (J.Labelled.Compd.Radiopharm, 31(8), 609, 1992; CA 117:171316w).

Substituted pyridinyl, pyurazinyl or pyrimidyl nitromethylene and nitroiminoimidazolidines and their synergistic mixtures are reported for moth proofing (EP 387663, 1989; CA 114:p201780 a). 2-nitroimino or cyano iminoimidazolidines and hexahydropyrimidine derivatives are reported as insecticides (JP 63156786, 1988; CA 110:p8210d). 1-diazinyl methyl-2-nitro methylene and 2-nitroiminoimidazolidines are reported as new potential insecticides against green leaf hoppers on rice seedling in spray applications (Nippon Noyaku Gakkaishi 18(1), 119, 1993; CA 119:111238d). N-nitroiminoimidazolidines derivatives of 2-chloropyridine-5-yl, 2-chlorothiazol-5-yl are reported as active ingredients of insecticides (JP 06122680, 1994; CA 121:p157642a & JP 06100557, 1994; CA 121 :255796y). N-nitroiminodithiocarbonate compounds serve as intermediates for insecticides and pharmaceuticals (U.S. Pat. No. 5,453,529, 1995; CA 124:p55973d). N-substituted alkyl, haloalkenyl, alkynyl, aralkyl, aromatic heterocyclymethyl compounds serve as insecticides (JP 02207083, 1990; CA 114:62097t). N-vinyl imidazolidine derivatives and 2-phenyl dicyano imidazoles are reported as insecticides and anthelminitics (EP 547557, 1993; CA 119:225953p and Ger.Offen. DE 19548914, 1994; CA 125: 142731n).

The discovery of new compounds for use as pesticides is still desired for effective crop protection.

OBJECTS OF THE INVENTION

The main object of the invention is to provide new compounds for use as pesticides for effective crop protection.

It is another object of the invention to provide new compounds for use as pesticides with good yield and selectivity.

It is a further object of the invention to provide a new compound 1-(2-chloro-5-methyl-3-pyridylmethyl)-2-nitroiminoimadozolidine of the class of nitroimino pyridyl derivatives for use as pesticide.

It is another object of the invention to provide a process for the preparation of a novel compound 1-(2-chloro-5-methyl-3-pyridylmethyl)-2-nitroiminoimidazolidine where the reaction time is short and the temperature conditions are mild.

SUMMARY OF THE INVENTION

Accordingly, the present invention relates to a novel compound 1-(2-chloro-5-methyl-3-pyridylmethyl)-2-nitroiminoimidazolidine of the formula 1 given below.

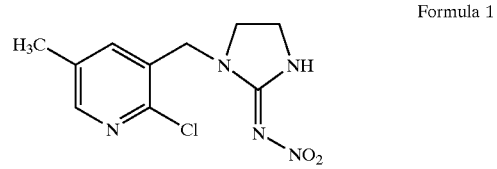

Formula 1

The present invention also relates to a process for the preparation of 1-(2-chloro-5-methyl-3-pyridylmethyl)-2-nitroiminoimidazolidine of the formula 1

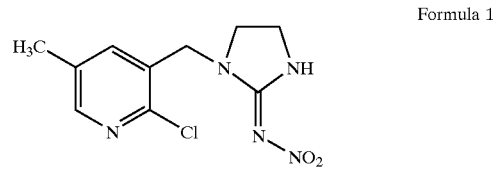

Formula 1

In one embodiment of the invention, the organic solvent used comprises acetonitrile.

In another embodiment of the invention, the base used comprises potassium carbonate.

In a further embodiment of the invention, the reaction is carried out for a time period in the range of 5 to 10 hours.

In yet another embodiment of the invention, the molar ratio of 2-chloro-3-chloromethyl-5-methyl pyridine to 2-nitroimino-1, 3-diazacyclopentane is in the range of 1:1–1.5, preferably 1:1.2.

In another embodiment of the invention, 2-chloro-3-chloromethyl-5-methyl pyridine is obtained by the sodium borohydride reduction of 2-chloro-5-methylpyridine-3-carbaldehyde with 88% yield.

In another embodiment of the invention, 2-chloro-3-chloromethyl-5-methyl pyridine is obtained by the sodium borohydride reduction of 2-chloro-5-methylpyridine-3-carbaldehyde with 88% yield.

DETAILED DESCRIPTION OF THE INVENTION

The invention will be described in detail with reference to the following examples, which are illustrative and should not be construed as limiting the scope of the invention in any manner.

EXAMPLE 1

2-chloro-3-chloromethyl-5-methylpyridine (1.3 g, 0.0076 moles) was added to a well-stirred material comprising of 2-nitroimino-1, 3-diazacyclopentane (1.18 g, 0.00912 moles), potassium carbonate (1.16 g, 0.0083 moles), cesium chloride (0.04 g, 0.00024 moles) in acetonitrile (10 ml) solvent at room temperature. The reaction mixture was refluxed for 5 hours. Solvent was removed under reduced pressure and the mass diluted with water (25 ml). The mass was then extracted with methylene chloride (2×50 ml) and the layers were separated. Organic layer was dried over sodium sulphate and solvent removed under reduced pressure. The residue obtained was subjected to chromatographic purification on silica gel to give 1-(2-chloro-5-methyl-3-pyridylmethyl)-2-nitroiminoimidazolidine in 90% yield. NMR (CDCl$_3$+DMSO d$_6$): δ2.38 (s, 3H, CH$_3$), 3.58 (t, 2H, N—CH$_2$), 3.74 (t, 2H, N—CH$_2$), 4.52 (s, 2H, CH$_2$), 7.54 (s, 1H, aromatic), 812 (s, 1H, aromatic), 8.86 (1H, NH). Mass: M+. 269.

EXAMPLE 2

2-chloro-3-chloromethyl-5-methylpyridine (1.3 g, 0.0076 moles) was added to a well-stirred material comprising 2-nitroimino-1, 3-diazacyclopentane (1.18 g, 0.00912 moles), potassium carbonate (1.16 g, 0.0083 moles), cesium chloride (0.04 g, 0.00024 moles) in acetonitrile (20 ml) solvent at room temperature. The reaction mixture was refluxed for 8 hours. The solvent was removed under reduced pressure and the mass diluted with water (25 ml). The mass was then extracted with methylene chloride (2×50 ml) and the layers were separated. Organic layer was dried over sodium sulphate and solvent removed under reduced pressure. The residue thus obtained was subjected to chromatographic purification on silica gel to give 1-(2-chloro-5-methyl-3-pyridylmethyl)2-nitroiminoimidazolidine in 90% yield.

EXAMPLE 3

Sodium borohydride (0.65 g, 0.0167 moles) was added slowly to a well-stirred solution of 2-chloro-5-methylpyridine-3-carbaldehyde (1.3 g, 0.0084 moles) in methanol (20 ml) at 0° C. temperature over a period of 15 minutes. The reaction mass was further stirred for 2 hours at the same temperature. The solvent was removed under reduced pressure and the mass was quenched with water (25 ml). The mass was extracted with ethyl acetate (2×50 ml) and the layers separated. The organic layer was removed under reduced pressure. The residue so obtained was subjected to chromatographic purification on silica gel to give 2-chloro-3-hydroxymethyl-5-methylpyridine as a solid in 88% yield.

NMR (CDCl$_3$): δ2.34 (s, 3H, CH$_3$), 3.7 (1H, OH), 4.68 (s, 2H, CH$_2$), 7.68 (s, 1H, aromatic), 8.04 (s, 1H, aromatic). Mass: M+. 157.

EXAMPLE 4

Thionyl chloride (2.73 g, 0.023 moles) was added slowly to a well-stirred solution of 2-chloro-3-hydroxymethyl-5-methylpyridine (1.2 g, 0.0076 moles) in methylenechloride (20 ml) at 0° C. temperature over a period of 20 minutes. The reaction mass was further stirred for 6 hours at the same temperature. The solvent and excess thionylchloride was removed under reduced pressure and the mass was quenched with water (25 ml). The mass was extracted with methylene chloride (2×50 ml) and the layers separated. The organic layer was dried over sodium sulphate and the solvent removed under reduced pressure. The residue so obtained was subjected to chromatographic purification on silica gel to give 2-chloro-3-chloromethyl-5-methylpyridine as a solid in 92% yield.

NMR (CDCl$_3$): δ2.36 (s, 3H, CH$_3$), 4.6 (s, 2H, CH$_2$), 7.62 (s, 1H, aromatic), 8.16 (s, 1H, aromatic). Mass: M+. 175.

ADVANTAGES OF THE INVENTION

1. The compound of the invention is a novel compound and is useful as a pesticide.
2. The yield of the compound is high.
3. The reaction is carried out at low temperature and short reaction times making the process cost effective.
4. Isolation of the product is simple.

We claim:

1. 1-(2-chloro-5-methyl-3-pyridylmethyl)-2-nitroiminoimidazolidine of the general formula 1

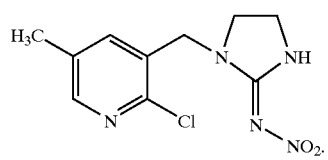

Formula 1

2. A process for the preparation of 1-(2-chloro-5-methyl-3-pyridylmethyl)-2-nitroiminoimidazolidine of the formula 1

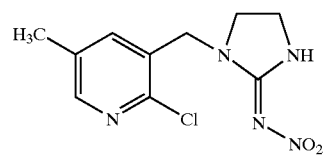

Formula 1 comprising reacting 2-chloro-3-chloromethyl-5-methyl pyridine and 2-nitroimino-1,3-diazacyclopentane in the presence of a base and an organic solvent.

3. A process as claimed in claim 2 wherein said base used comprises potassium carbonate.

4. A process as claimed in claim 2 wherein the organic solvent used comprises acetonitrile.

5. A process as claimed in claim 2 wherein the reaction is carried out for a time period in the range of 5 to 10 hours.

6. A process as claimed in claim 2 wherein the molar ratio of 2-chloro-3-chloromethyl-5-methyl pyridine to 2-nitroimino-1,3-diazacyclopentane is in the range of 1:1–1.5.

7. A process as claimed in claim 6 wherein the molar ratio of 2-chloro-3-chloromethyl-5-methyl pyridine to 2-nitroimino-1,3-diazacyclopentane is 1:1.2.

8. A process for the preparation of 1-(2-chloro-5-methyl-3-pyridylmethyl)-2-nitroiminoimidazolidine of the formula 1

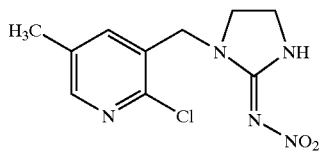

Formula 1

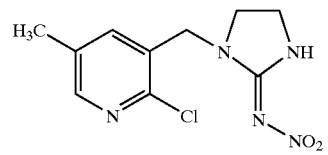

Formula 1 comprising reacting 2-chloro-3-hydroxymethyl-5-methylpyridine with thionyl chloride to give 2-chloro-3-chloromethyl-5-methylpyridine, followed by reacting the 2-chloro-3-chloromethyl-5-methylpyridine thus obtained with 2-nitroimino-1,3-diazacyclopentane in the presence of a base and an organic solvent, to give 1-(2-chloro-5-methyl-3-pyridylmethyl)-2-nitroiminoimidazolidine.

9. A process for the preparation of 1-(2-chloro-5-methyl-3-pyridylmethyl)-2-nitroiminoimidazolidine of the formula 1 comprising reducing 2-chloro-5-methylpyridine-3-carbaldehyde with sodium borohydride to give 2-chloro-3-hydroxymethyl-5-methylpyridine, followed by reacting the 2-chloro-3-hydroxymethyl-5-methylpyridine thus obtained with thionyl chloride to give 2-chloro-3-chloromethyl-5-methylpyridine, followed by reacting the 2-chloro-3-chloromethyl-5-methylpyridine thus obtained with 2-nitroimino-1,3-diazacyclopentane in the presence of a base and an organic solvent, to give 1-(2-chloro-5-methyl-3-pyridylmethyl)-2-nitroiminoimidazolidine.

* * * * *